United States Patent [19]

Terahara et al.

[11] Patent Number: 4,866,093
[45] Date of Patent: Sep. 12, 1989

[54] M-4 AND ISO M-4 DERIVATIVES, THEIR PREPARATION AND COMPOSITIONS CONTAINING THEM

[75] Inventors: Akira Terahara; Minoru Tanaka, both of Tokyo, Japan

[73] Assignee: Sankyo Company Limited, Tokyo, Japan

[21] Appl. No.: 590,733

[22] Filed: Mar. 19, 1984

Related U.S. Application Data

[62] Division of Ser. No. 375,333, May 5, 1982, Pat. No. 4,451,481.

[30] Foreign Application Priority Data

May 11, 1981 [JP] Japan .................................. 56-70497

[51] Int. Cl.$^4$ ................... A61K 31/215; A61K 31/22; C07C 69/33; C07C 69/675
[52] U.S. Cl. ..................................... 514/510; 536/55.2; 544/109; 548/344; 548/543; 556/131; 556/147; 556/183; 560/38; 560/119; 560/155; 560/156; 560/256
[58] Field of Search ............... 560/256, 119, 155, 171, 560/38; 260/501.1, 501.11; 548/543, 344; 544/109; 536/55.2; 556/147, 114, 131, 183; 514/510

[56] References Cited

U.S. PATENT DOCUMENTS

| | | | |
|---|---|---|---|
| 4,342,767 | 8/1982 | Albers-Schonberg | 560/119 |
| 4,346,227 | 8/1982 | Terahara et al. | 560/119 |
| 4,420,491 | 12/1983 | Albers-Schonberg | 560/119 |
| 4,438,277 | 3/1984 | Terahara et al. | 560/119 |
| 4,444,784 | 4/1984 | Hoffman et al. | 549/292 |

Primary Examiner—Werren B. Lone
Attorney, Agent, or Firm—Frishauf, Holtz, Goodman & Woodward

[57] ABSTRACT

The dihydro-M-4 and dihydro-IsoM-4 hydroxy carboxylic acids of the formula (II):

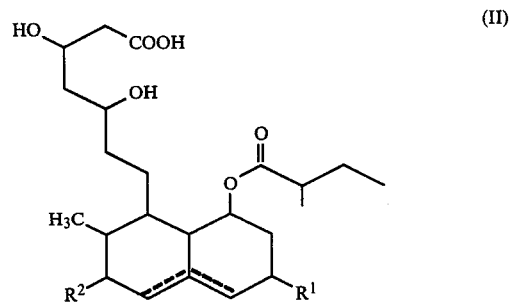

wherein one of $R^1$ represents a hydrogen atom and the other represents a hydroxy group and wherein the structure shown as

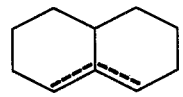

represents a structure of formula

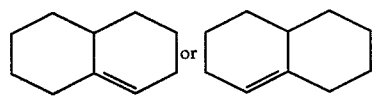

and the salts and esters of said acids. The invention also provides pharmaceutical compositions containing said acids, salts and/or esters which are useful for inhibiting cholesterol biosynthesis in the liver.

22 Claims, 3 Drawing Sheets

M-4 AND ISO M-4 DERIVATIVES, THEIR PREPARATION AND COMPOSITIONS CONTAINING THEM

This is a division of application Ser. No. 375,333, filed May 5, 1982.

BACKGROUND TO THE INVENTION

The present invention relates to a series of new derivatives of M-4 and IsoM-4, to processes for preparing them and to pharmaceutical compositions containing them.

M-4 and IsoM-4, which are described in U.S. patent application Ser. No. 270,846, filed 5th June 1981, to A. Terahara and M. Tanaka which issued as U.S. Pat. No. 4,346,227, when in the form of their lactones, have the formulae:

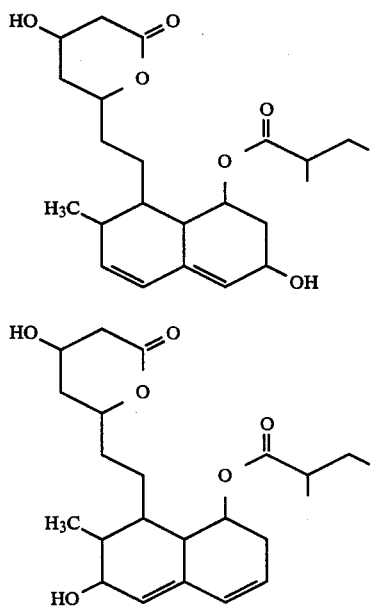

respectively. The formulae given above show the compounds in their lactone form; of course, under appropriate conditions, the lactone can be hydrated to give the corresponding hydroxycarboxylic acid.

M-4 and IsoM-4 are amongst a number of compounds which may be derived from the group of compounds collectively designated ML-236 and described, for example, in U.S. Patent Specification No. 3,983,140. Other compounds having a similar structure and collectively designated MB-530 have been discovered and are described, for example, in United Kingdom Specifications Nos. 2,046,737, 2,049,664 and 2,055,100, and derivatives of both the ML-236 and MB-530 compounds are described, for example, in United Kingdom Patent Specification No. 2,075,013. Of the many compounds there are known which have structures of the ML-236 or MB-530 type, most have shown some ability to inhibit the biosynthesis of cholesterol and some have shown this ability to a sufficient degree that they might be of value in the treatment of such disorders as hyperlipaemia (especially hypercholesteraemia) and arteriosclerosis.

We have now discovered a series of compounds which are derivatives of M-4 and IsoM-4 and which, whilst retaining the ability of their parent compounds to inhibit the biosynthesis of cholesterol, are far less readily deactivated in vivo than are the parent compounds.

BRIEF SUMMARY OF INVENTION

The compounds of the invention are dihydro-M-4 and dihydro-IsoM-4 lactones which have the formula (I):

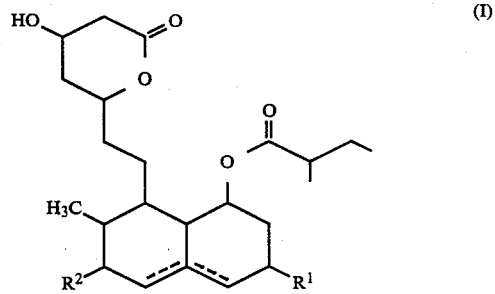

and their corresponding free carboxylic acids, which may be represented by formula (II):

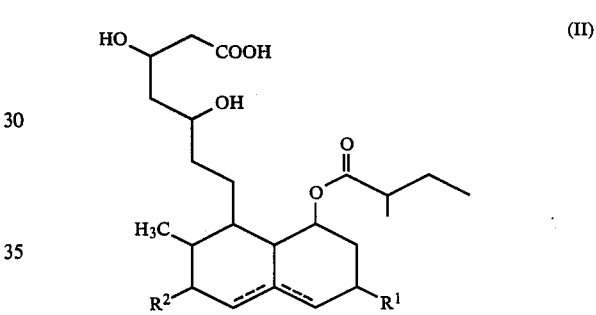

(in which one of $R^1$ and $R^2$ represents a hydrogen atom and the other represents a hydroxy group and in which the structure shown as

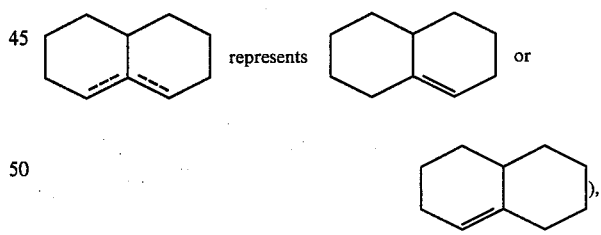

and salts and esters of the carboxylic acids.

Those compounds of formulae (I) and (II) in which $R^1$ represents a hydroxy group and $R^2$ represents a hydrogen atom are collectively referred to as "dihydro-M-4" and those compounds of formulae (I) and (II) in which $R^1$ represents a hydrogen atom and $R^2$ represents a hydroxy group are collectively referred to as "dihydro-IsoM-4". The compounds of formula (I) are referred to as "dihydro-M-4 lactone" or "dihydro-IsoM-4 lactone" and the compounds of formula (II) are referred to as "dihydro-M-4 carboxylic acid" or "dihydro-IsoM-4 carboxylic acid".

Compounds in which the structure shown as represents the group 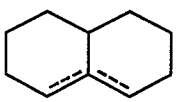

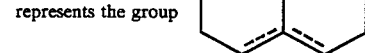

are known as Δ⁴ compounds, whilst compounds in which this structure represents the group

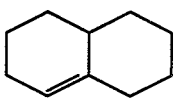

are known as Δ⁴ᵃ compounds. Thus, dihydro-Δ⁴-M-4 lactone may be represented by the formula (Ia):

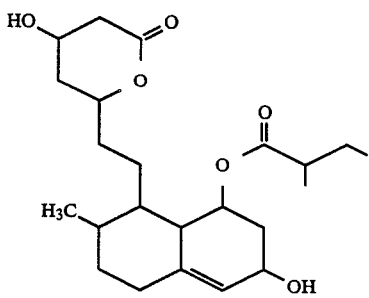

dihydro-Δ⁴ᵃ-M-4 lactone may be represented by the formula (Ib):

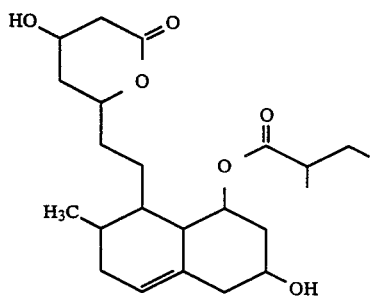

dihydro-Δ⁴-IsoM-4 lactone may be represented by the formula (Ic):

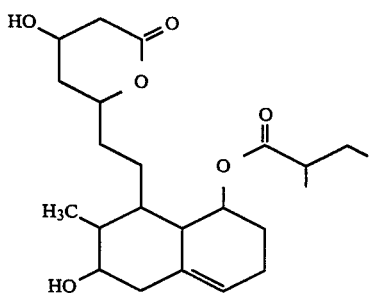

and dihydro-Δ⁴ᵃ-IsoM-4 lactone may be represented by formula (Id):

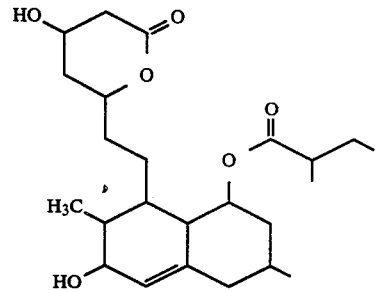

The carboxylic acids, dihydro-Δ⁴-M-4 carboxylic acid, dihydro-Δ⁴ᵃ-M-4 carboxylic acid, dihydro-Δ⁴-IsoM-4 carboxylic acid and dihydro-Δ⁴ᵃ-IsoM-4 carboxylic acid, of formula (II) may, of course, also be represented by formulae corresponding to (Ia)–(Id).

The invention also provides processes for preparing dihydro-M-4 and dihydro-IsoM-4 by the catalytic reduction of M-4 or IsoM-4, respectively, and for the preparation of salts and esters by salification or esterification of dihydro-M-4 or dihydro-IsoM-4.

The catalytic reduction reaction normally produces a mixture of the respective Δ⁴ and Δ⁴ᵃ compounds; these may be separated or used as a mixture. Thus, the present invention provides both the individual compounds and mixtures of the respective Δ⁴ and Δ⁴ᵃ compounds.

The invention also provides a pharmaceutical composition comprising an effective amount of an antihyperlipaemic agent in admixture with a pharmaceutically acceptable carrier or diluent, wherein the antihyperlipaemic agent is at least one compound selected from compounds of formula (I), compounds of formula (II) and salts and esters thereof.

DETAILED DESCRIPTION OF INVENTION

Figure 1:
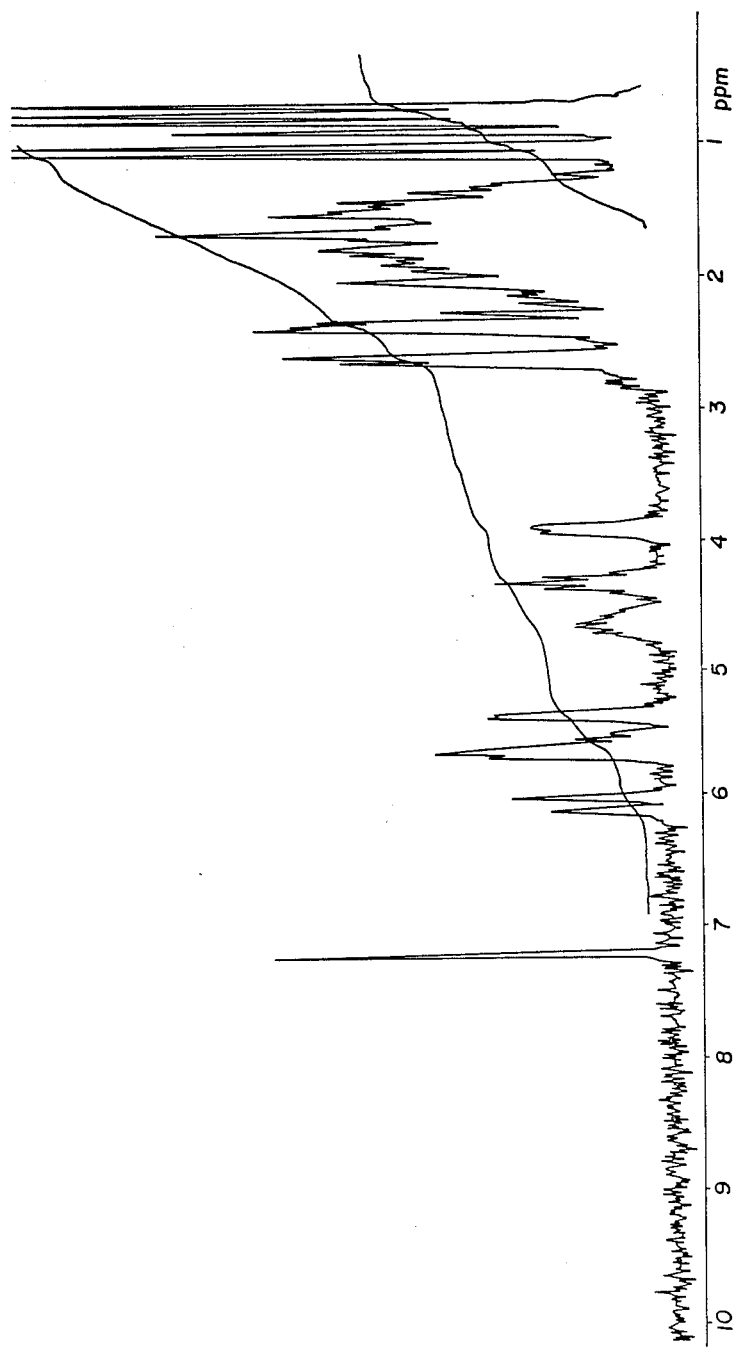

The salts of dihydro-M-4 or dihydro-IsoM-4 carboxylic acids may be metal salts, ammonium salts or salts with organic amines or amino acids.

Metal salts of dihydro-M-4 carboxylic acid and of dihydro-IsoM-4 carboxylic acid may be represented by formula (III):

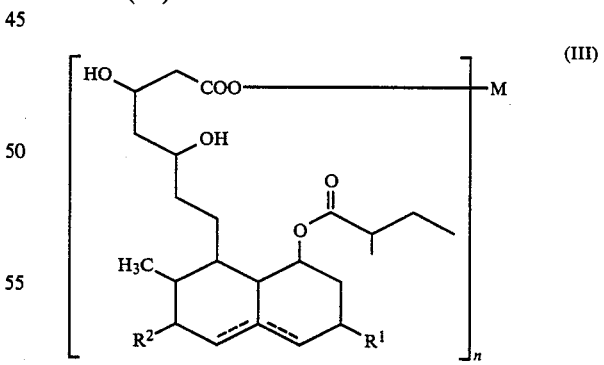

(in which R¹, R² and the structure

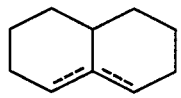

are as defined above, M represents a metal atom and n represents the valency of the metal atom). Examples of metals which may be represented by M in these salts include: alkali metals, such as sodium or potassium; alkaline earth metals, such as calcium or magnesium; and other metals, such as aluminium, iron, zinc, nickel or cobalt. Of these metals, the alkali metals, alkaline earth metals and aluminium are preferred, sodium, calcium and aluminium being most preferred.

The ammonium, organic amine and amino acid salts of dihydro-M-4 carboxylic acid and of dihydro-IsoM-4 carboxylic acid may be represented by formula (IV):

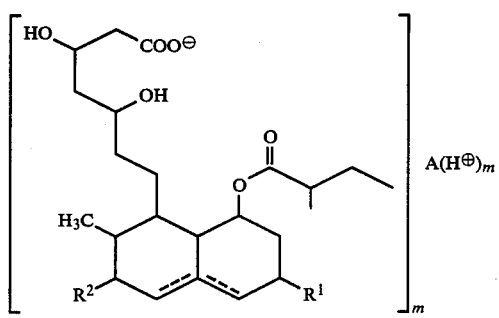

(in which $R^1$, $R^2$ and the structure

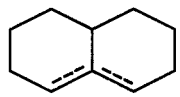

are as defined above, A represents ammonia, an amino acid or an organic amine, and m is an integer). The integer represented by m is preferably 1, that is to say the amine or amino acid represented by A is preferably monoacidic.

Examples of amino acids which may be represented by A in the above formula (IV) include such basic amino acids as arginine, lysine, histidine, 2,4-diaminobutyric acid, or ornithine.

When A represents an organic amine, it is preferably a monoamine and may be an aliphatic, aromatic, alicyclic, heterocyclic or carbohydrate monoamine. Examples include: primary alkylamines, such as octylamine, t-octylamine or 2-ethylhexylamine; primary, secondary and tertiary $C_7$ or $C_8$ aralkylamines, such as benzylamine, α-methyl-benzylamine, phenethylamine, dibenzylamine, N-methylbenzylamine, N,N-dimethylbenzylamine, N,N-diethylbenzylamine, N-ethyl-N-methylbenzylamine or tribenzylamine; primary, secondary or tertiary $C_5$–$C_7$ saturated alicyclic amines, such as cyclopentylamine, cyclohexylamine, cycloheptylamine, N-methylcyclopentylamine, N-ethylcyclohexylamine, N-ethylcycloheptylamine, dicyclohexylamine, N,N-dimethylcyclopentylamine, N,N-dimethylcyclohexylamine or N,N-diethylcycloheptylamine; 5 or 6 membered heterocyclic amines having a single nitrogen atom as the hetero atom, such as pyrrolidine, N-methylpyrrolidine, piperidine or N-methylpiperidine; morpholine; $C_1$–$C_3$ alkyl esters of aliphatic or aromatic amino acids, such as leucine methyl ester, diethyl glutamate, phenylglycine ethyl ester, β-phenylalanine propyl ester or β-phenylalanine methyl ester; and amine derivatives of carbohydrates, such as glucosamine.

Where the amine acids and amines mentioned above can exist in the form of stereoisomers or optical isomers, it is possible to use any of the isomers or mixtures thereof.

Preferred amines are t-octylamine, benzylamine, dibenzylamine, N,N-dimethylbenzylamine, cyclohexylamine, dicyclohexylamine, N,N-dimethylcyclohexylamine, N-methylpyrrolidine, morpholine, L-leucine alkyl esters, dialkyl L-glutamates, D-phenylglycine alkyl esters and D-glucosamine; of which the most preferred amines are t-octylamine, dibenzylamine, dicyclohexylamine, morpholine, D-phenylglycine alkyl esters and D-glucosamine.

The esters of dihydro-M-4 carboxylic acid and the dihydro-IsoM-4 carboxylic acid may be represented by formula (V):

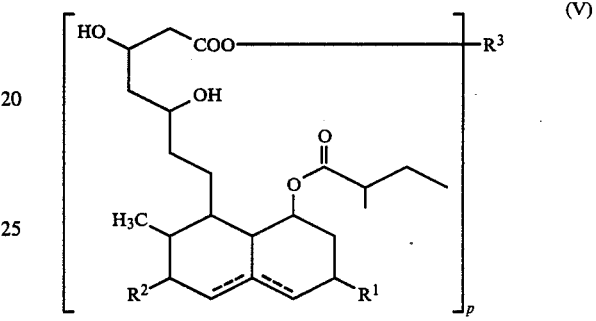

(in which $R^1$, $R^2$ and the structure

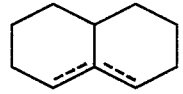

are as defined above, $R^3$ represents the alcoholic moiety of an ester and p represents the valency of $R^3$).

Where p represents 1, $R^3$ preferably represents an alkyl group, an unsubstituted benzyl group, a substituted benzyl group having at least one substituent selected from alkyl groups, alkoxy groups and halogen atoms, an unsubstituted phenacyl group or a substituted phenacyl group having at least one substituent selected from alkyl groups, alkoxy groups and halogen atoms.

Where $R^3$ represents an alkyl group, this may be a straight or branched chain group and preferably has from 1 to 6 carbon atoms. Examples of such a group include the methyl, ethyl, propyl, isopropyl, butyl, pentyl and hexyl groups.

Where $R^3$ represents a benzyl group, this may be unsubstituted or substituted, the substituents preferably being $C_1$ or $C_2$ alkyl or alkoxy groups or halogen atoms. One or more, preferably one, substituents are possible and, if there is more than one substituent, these may be the same or different. Examples of such benzyl groups include the benzyl, 2-methylbenzyl, 3-methylbenzyl, 4-methylbenzyl, 2-ethylbenzyl, 3-ethylbenzyl, 4-ethylbenzyl, 2-methoxybenzyl, 3-methoxybenzyl, 4-methoxybenzyl, 2-ethoxybenzyl, 3-ethoxybenzyl, 4-ethoxybenzyl, 2-chlorobenzyl, 3-chlorobenzyl, 4-chlorobenzyl, 2-bromobenzyl, 3-bromobenzyl and 4-bromobenzyl groups.

$R^3$ may represent an unsubstituted or substituted phenacyl group, in which the substituents are preferably $C_1$ or $C_2$ alkyl or alkoxy groups or halogen atoms. One or more, preferably one, substituents are possible and, where there is more than one substituent, these may be the same or different. Examples of such phenacyl groups include the phenacyl, 2-methylphenacyl, 3-methylphenacyl, 4-methylphenacyl, 2-ethylphenacyl, 3-ethylphenacyl, 4-ethylphenacyl, 2-methoxyphenacyl, 3-methoxyphenacyl, 4-methoxyphenacyl, 2-ethoxyphenacyl, 3-ethoxyphenacyl, 4-ethoxyphenacyl, 2-chlorophenacyl, 3-chlorophenacyl, 4-chlorophenacyl, 2-bromophenacyl, 3-bromophenacyl and 4-bromophenacyl groups.

Where p is 2, $R^3$ represents a bivalent alcoholic moiety, preferably a $C_2$–$C_6$ alkylene or alkylidene group, for example, an ethylene, ethylidene, propylene, propylidene, trimethylene, tetramethylene, butylidene, pentamethylene or pentylidene group, as well as such groups having one or more substituents, e.g. hydroxy groups, halogen atoms, or trifluoromethyl groups.

Where p is 3, $R^3$ represents a trivalent alcoholic moiety and it is preferably a saturated aliphatic hydrocarbon group having from 2 to 6 carbon atoms and optionally one or more substituents, e.g. hydroxy groups, halogen atoms or trifluoromethyl groups.

We prefer that p should be 1 and that $R^3$ should represent an alkyl group (most preferably methyl, ethyl, propyl, isopropyl, butyl or hexyl), an optionally substituted benzyl group (most preferably benzyl, 4-methylbenzyl, 4-methoxybenzyl or 4-chlorobenzyl) or an optionally substituted phenacyl group (most preferably phenacyl, 4-methylphenacyl, 4-methoxyphenacyl or 4-bromophenacyl).

Representative examples of compounds of the invention are given in the following list:
1. Dihydro-M-4.
2. Dihydro-IsoM-4.
3. Sodium dihydro-M-4 carboxylate.
4. Sodium dihydro-IsoM-4 carboxylate.
5. Calcium di(dihydro-M-4 carboxylate).
6. Calcium di(dihydro-IsoM-4 carboxylate).
7. Aluminium tri(dihydro-M-4 carboxylate).
8. Aluminium tri(dihydro-IsoM-4 carboxylate).
9. Arginine dihydro-M-4 carboxylate.
10. Arginine dihydro-IsoM-4 carboxylate.
11. Lycine dihydro-M-4 carboxylate.
12. Lycine dihydro-IsoM-4 carboxylate.
13. Histidine dihydro-M-4 carboxylate.
14. Histidine dihydro-IsoM-4 carboxylate.
15. The 2,4-diaminobutyric acid salt of dihydro-M-4.
16. The 2,4-diaminobutyric acid salt of dihydro-IsoM-4.
17. Ornithine dihydro-M-4 carboxylate.
18. Ornithine dihydro-IsoM-4 carboxylate.
19. t-Octylamine dihydro-M-4 carboxylate.
20. t-Octylamine dihydro-IsoM-4 carboxylate.
21. Dibenzylamine dihydro-M-4 carboxylate.
22. Dibenzylamine dihydro-IsoM-4 carboxylate.
23. Dicyclohexylamine dihydro-M-4 carboxylate.
24. Dicyclohexylamine dihydro-IsoM-4 carboxylate.
25. Morpholine dihydro-M-4 carboxylate.
26. Morpholine dihydro-IsoM-4 carboxylate.
27. Aluminium di(dihydro-M-4 carboxylate) hydroxide.
28. Aluminium di(dihydro-IsoM-4 carboxylate) hydroxide.
29. Glucosamine dihydro-M-4 carboxylate.
30. Glucosamine dihydro-IsoM-4 carboxylate.
31. The dimethyl glutamate salt of dihydro-M-4.
32. The diethyl glutamate salt of dihydro-M-4.
33. The dipropyl glutamate salt of dihydro-M-4.
34. The diisopropyl glutamate salt of dihydro-M-4.
35. The dibutyl glutamate salt of dihydro-M-4.
36. The di-sec-butyl glutamate salt of dihydro-M-4.
37. The di-t-butyl glutamate salt of dihydro-M-4.
38. The dipentyl glutamate salt of dihydro-M-4.
39. The diisopentyl glutamate salt of dihydro-M-4.
40. The di-t-pentyl glutamate salt of dihydro-M-4.
41. The dimethyl glutamate salt of dihydro-IsoM-4.
42. The diethyl glutamate salt of dihydro-IsoM-4.
43. The dipropyl glutamate salt of dihydro-IsoM-4.
44. The diisopropyl glutamate salt of dihydro-IsoM-4.
45. The dibutyl glutamate salt of dihydro-IsoM-4.
46. The di-sec-butyl glutamate salt of dihydro-IsoM-4.
47. The di-t-butyl glutamate salt of dihydro-IsoM-4.
48. The dipentyl glutamate salt of dihydro-IsoM-4.
49. The diisopentyl glutamate salt of dihydro-Iso-M-4.
50. The di-t-pentyl glutamate salt of dihydro-Iso-M-4.
51. Methyl dihydro-M-4 carboxylate.
52. Methyl dihydro-IsoM-4 carboxylate.
53. Ethyl dihydro-M-4 carboxylate.
54. Ethyl dihydro-IsoM-4 carboxylate.
55. Propyl dihydro-M-4 carboxylate.
56. Propyl dihydro-IsoM-4 carboxylate.
57. Isopropyl dihydro-M-4 carboxylate.
58. Isopropyl dihydro-IsoM-4 carboxylate.
59. Butyl dihydro-M-4 carboxylate.
60. Butyl dihydro-IsoM-4 carboxylate.
61. Hexyl dihydro-M-4 carboxylate.
62. Hexyl dihydro-IsoM-4 carboxylate.
63. Benzyl dihydro-M-4 carboxylate.
64. Benzyl dihydro-IsoM-4 carboxylate.
65. 4-Methylbenzyl dihydro-M-4 carboxylate.
66. 4-Methylbenzyl dihydro-IsoM-4 carboxylate.
67. 4-Methoxybenzyl dihydro-M-4 carboxylate.
68. 4-Methoxybenzyl dihydro-IsoM-4 carboxylate.
69. 4-Chlorobenzyl dihydro-M-4 carboxylate.
70. 4-Chlorobenzyl dihydro-IsoM-4 carboxylate.
71. Phenacyl dihydro-M-4 carboxylate.
72. Penacyl dihydro-IsoM-4 carboxylate.
73. 4-Methylphenacyl dihydro-M-4 carboxylate.
74. 4-Methylphenacyl dihydro-IsoM-4 carboxylate.
75. 4-Methoxyphenacyl dihydro-M-4 carboxylate.
76. 4-Methoxyphenacyl dihydro-Iso-M-4 carboxylate.
77. 4-Bromophenacyl dihydro-M-4 carboxylate.
78. 4-Bromophenacyl dihydro-IsoM-4 carboxylate.
79. The methyl ester of phenylglycine dihydro-M-4 carboxylate.
80. The ethyl ester of phenylglycine dihydro-M-4 carboxylate.
81. The propyl ester of phenylglycine dihydro-M-4 carboxylate.
82. The isopropyl ester of phenylglycine dihydro-M-4 carboxylate.
83. The butyl ester of phenylglycine dihydro-M-4 carboxylate.
84. The sec-butyl ester of phenylglycine dihydro-M-4 carboxylate.
85. The t-butyl ester of phenylglycine dihydro-M-4 carboxylate.
86. The pentyl ester of phenylglycine dihydro-M-4 carboxylate.
87. The isopentyl ester of phenylglycine dihydro-M-4 carboxylate.
88. The t-pentyl ester of phenylglycine dihydro-M-4 carboxylate.
89. The methyl ester of phenylglycine dihydro-IsoM-4 carboxylate.
90. The ethyl ester of phenylglycine dihydro-IsoM-4 carboxylate.

91. The propyl ester of phenylglycine dihydro-IsoM-4 carboxylate.
92. The isopropyl ester of phenylglycine dihydro-IsoM-4 carboxylate.
93. The butyl ester of phenylglycine dihydro-IsoM-4 carboxylate.
94. The sec-butyl ester of phenylglycine dihydro-IsoM-4 carboxylate.
95. The t-butyl ester of phenylglycine dihydro-IsoM-4 carboxylate.
96. The pentyl ester of phenylglycine dihydro-IsoM-4 carboxylate.
97. The isopentyl ester of phenylglycine dihydro-IsoM-4 carboxylate.
98. The t-pentyl ester of phenylglycine dihydro-IsoM-4 carboxylate.

The above compounds all exist as both $\Delta^4$ and $\Delta^{4a}$ isomers and may be provided as individual isomers or as mixtures thereof.

Of the compounds of the invention, the most preferred are the sodium salts, i.e. Compounds Nos. 3 and 4 of the above list.

The compounds of the invention have been found to inhibit cholesterol biosynthesis in the liver and thus may be used for the treatment of hypercholesteraemia or the prevention of arteriosclerosis, in the same way as are the compounds disclosed in U.S. patent application Ser. No. 256,243, filed 21st Apr. 1981 now U.S. Pat. No. 4,361,515, or U.S. patent application Ser. No. 270,846, filed 5th June 1981 now U.S. Pat. No. 4,346,227, and the compounds of the invention show an ability to inhibit cholesterol biosynthesis which is broadly comparable with that exhibited by the compounds disclosed in these two U.S. Patent Applications. However, the compounds of the invention have the significant advantage over the compounds disclosed in the aforementioned U.S. Patent Specifications that they are metabolised with much greater difficulty after administration and are thus less readily deactivated; this means that the activity of the compounds of the invention is more persistent and the compounds are thus expected to be of greater effectiveness.

The inhibitory activities of certain of the compounds of the invention, in terms of the concentration in μg/ml required to inhibit cholesterol biosynthesis by 50% [measured by the method described in the Journal of Biological Chemistry, 234, 2835 (1959)], are as follows:

| | |
|---|---|
| dihydro-$\Delta^4$-M-4 lactone | 0.032 |
| sodium dihydro-$\Delta^4$-M-4 carboxylate | 0.013 |
| methyl dihydro-$\Delta^4$-M-4 carboxylate | 0.016 |
| dihydro-$\Delta^4$-IsoM-4 lactone | 0.018 |
| sodium dihydro-$\Delta^4$-IsoM-4 carboxylate | 0.0063 |
| methyl dihydro-$\Delta^4$-IsoM-4 carboxylate | 0.012 |

The compounds of the invention may be administered by any conventional means, for example parenterally (e.g. by subcutaneous, intravenous or intramuscular injection) or orally (e.g. in the form of tablets, capsules, powders or granules). The adult daily dose will, of course, vary, depending upon the age, body weight and condition of the patient, as well as upon the route and times of administration, but, in general, the compounds of the invention are preferably administered in an amount of from 5 to 50 milligrams per day, for adults, in a single dose or in divided doses.

The compounds of the invention may be prepared by a variety of processes, all ultimately starting from M-4 or IsoM-4, which may be prepared as a microbial metabolite of ML-236B, and this, in turn, may be prepared as described in United Kingdom Patent Specification No. 1,453,425. The preparation of M-4 and IsoM-4 from ML-236B is described in more detail in Preparations 1 and 2 hereafter, and is also described in U.S. patent application Ser. No. 270,846, filed 5th June 1981.

Method 1

Compounds of formula (I) or (II), that is to say dihydro-M-4 or dihydro-IsoM-4 lactone or dihydro-M-4 or dihydro-IsoM-4 carboxylic acid, respectively, may be prepared by catalytic reduction, of the corresponding M-4 or IsoM-4 compound in a suitable solvent. The nature of the solvent is not critical, provided that it has no adverse effect upon the reaction. Suitable solvents include, for example, alcohols (such as methanol, ethanol or isopropanol) and ethers (such as tetrahydrofuran), any of which may be used in admixture with water. Examples of suitable catalysts include platinum oxide, rhodium colloids, Raney nickel, nickel boride and palladium, of which palladium catalysts are preferred. The reaction is preferably effected at or below ambient temperature, e.g. about 25° C. The hydrogen is preferably employed at atmospheric pressure.

The palladium used as catalyst is preferably supported on a carrier, suitable carriers including active carbon, barium sulphate, alumina and calcium carbonate. The most preferred carriers are active carbon and barium sulphate. The quantity of palladium in the supported catalyst may vary over a wide range, e.g. from 1 to 10%, more preferably from 5 to 10%, by weight of the supported catalyst.

There is, of course, a risk that, if the hydrogenation reaction is allowed to go too far, a significant proportion of the corresponding tetrahydro compound will be produced. However, by using the preferred catalyst system and preferred reaction conditions, this risk can be minimized.

Method 2

Compounds of formula (III), that is to say metal salts of dihydro-M-4 or dihydro-IsoM-4 carboxylic acids, may be prepared, for example, by the method described in United Kingdom Patent Specification No. 1,555,831 for the preparation of metal salts of ML-236B carboxylic acid.

Method 3

Amino acid salts of dihydro-M-4 or of dihydro-IsoM-4, that is to say compounds of formula (IV) in which A represents an amino acid, may be prepared from dihydro-M-4 or dihydro-IsoM-4, respectively, as described in United Kingdom Patent Specification No. 1,555,831.

Method 4

Amine salts of dihydro-M-4 or of dihydro-IsoM-4, that is to say compounds of formula (IV) in which A represents an organic amine or ammonia, may be prepared from dihydro-M-4 or from dihydro-IsoM-4 by the method described in Japanese Patent Application No. 56-8696, filed 23rd Jan. 1981. This comprises reacting an alkali metal carboxylate of dihydro-M-4 or dihydro-IsoM-4 such as the sodium carboxylate with a mineral acid (e.g. hydrochloric acid) salt of ammonia or an organic amine in a suitable solvent. The nature of the solvent is not critical, provided that it has no adverse effect upon the reaction, aqueous solvents being preferred. Examples include water itself and mixtures of water with one or more organic solvents, such as alcohols (e.g. methanol or ethanol) or ketones (e.g. acetone). The amount of amine salt is preferably equimolar or a slight molar excess, with respect to the metal carboxylate, e.g. a molar ratio amine salt:metal carboxylate of from 1:1 to 1.2:1. The reaction is preferably effected at a pH value of from 7.0 to 8.5 and a temperature of ambient or below, e.g. from 0° C. to 10° C., more preferably from 5° C. to 10° C. After the reaction, the resulting salt may be separated from the reaction mixture by extraction with a suitable solvent, such as ethyl acetate.

Method 5

Compounds of formula (V), that is to say esters of dihydro-M-4 or dihydro-IsoM-4 carboxylic acids, may be prepared by esterification of dihydro-M-4 or of dihydro-IsoM-4, as described in United Kingdom Patent Specification No. 1,555,831 in relation to the preparation of esters of ML-236B carboxylic acid, by reaction of dihydro-M-4 or of dihydro-IsoM-4 with an alcohol in the presence of a suitable catalyst.

Method 6

Compounds of formula (V) may also be prepared by reacting dihydro-M-4 carboxylic acid or dihydro-IsoM-4 carboxylic acid with a diazo compound, preferably diazomethane or a C-substituted diazomethane, as described in United Kingdom Patent Specification No. 1,555,831.

Method 7

Dihydro-M-4 lactone and dihydro-IsoM-4 lactone may be converted to the corresponding carboxylic acids by neutralisation.

The compounds of the invention can exist in the form of various optical isomers and the present invention envisages both the individual isomers and mixtures thereof.

The preparation of the compounds of the invention is illustrated by the following non-limiting Examples, whilst the preparation of M-4 and IsoM-4, the starting materials for the preparation of the compounds of the invention, is illustrated in the following Preparations 1 and 2.

Preparation 1

Preparation of IsoM-4

Twenty 500 milliliter Sakaguchi flasks, each containing 100 milliliter of a medium having the composition described below, were innoculated with spores of *Absidia coerulea* IFO 4423. The flasks were subjected to shaking culture at 120 strokes per minute (s.p.m.) and 26° C. for 2 days. At the end of this time, the sodium salt of ML-236B was added to each of the flasks to a final concentration of 0.05% w/v. Cultivation was continued at 120 s.p.m. and 26° C. for a further 5 days.

The composition of the medium was (percentages are w/v):

| | |
|---|---|
| Glucose | 2.0% |
| K$_2$HPO$_4$ | 0.15% |
| MgSO$_4$.7H$_2$O | 0.15% |
| NH$_4$NO$_3$ | 0.1% |
| Peptone | 0.1% |
| Corn steep liquor | 0.2% |
| Yeast extract | 0.1% |
| ZnSO$_4$.7H$_2$O | 0.001% |
| Tap water | the balance |
| (Adjusted to pH 7.0). | |

After completion of the cultivation, the reaction liquor was filtered and the pH of the filtrate was adjusted to a value of 3 by the addition of trifluoroacetic acid. The resulting mixture was then extracted with three 1 liter portions of ethyl acetate, to give extracts containing M-4 and M-3, as well as the desired IsoM-4. The combined extracts were washed with a saturated aqueous solution of sodium chloride and then evaporated to dryness to give a powder containing the lactones of the three compounds.

This powder was then subjected to column chromatography using a Lobar column (Merck Si 60, size A) and the IsoM-4 lactone fraction was eluted using a 1:1 by volume mixture of benzene and ethyl acetate. Evaporation of the solvent yielded 198 milligrams of IsoM-4 lactone, which was further purified using a Lobar column (Merck RP-8, size A), eluted with 35% v/v aqueous acetonitrile, to give 82 milligrams of pure IsoM-4 lactone, having the following characteristics:

1. Nuclear magnetic resonance spectrum:

The nuclear magnetic resonance spectrum measured at 100 MHz in deuterochloroform using tetramethylsilane as the internal standard is shown in FIG. 1 of the accompanying drawings.

2. Ultraviolet absorption spectrum (methanol solution)

$\lambda_{max}$ nm: 229, 234.8, 244.5.

Figure 2:
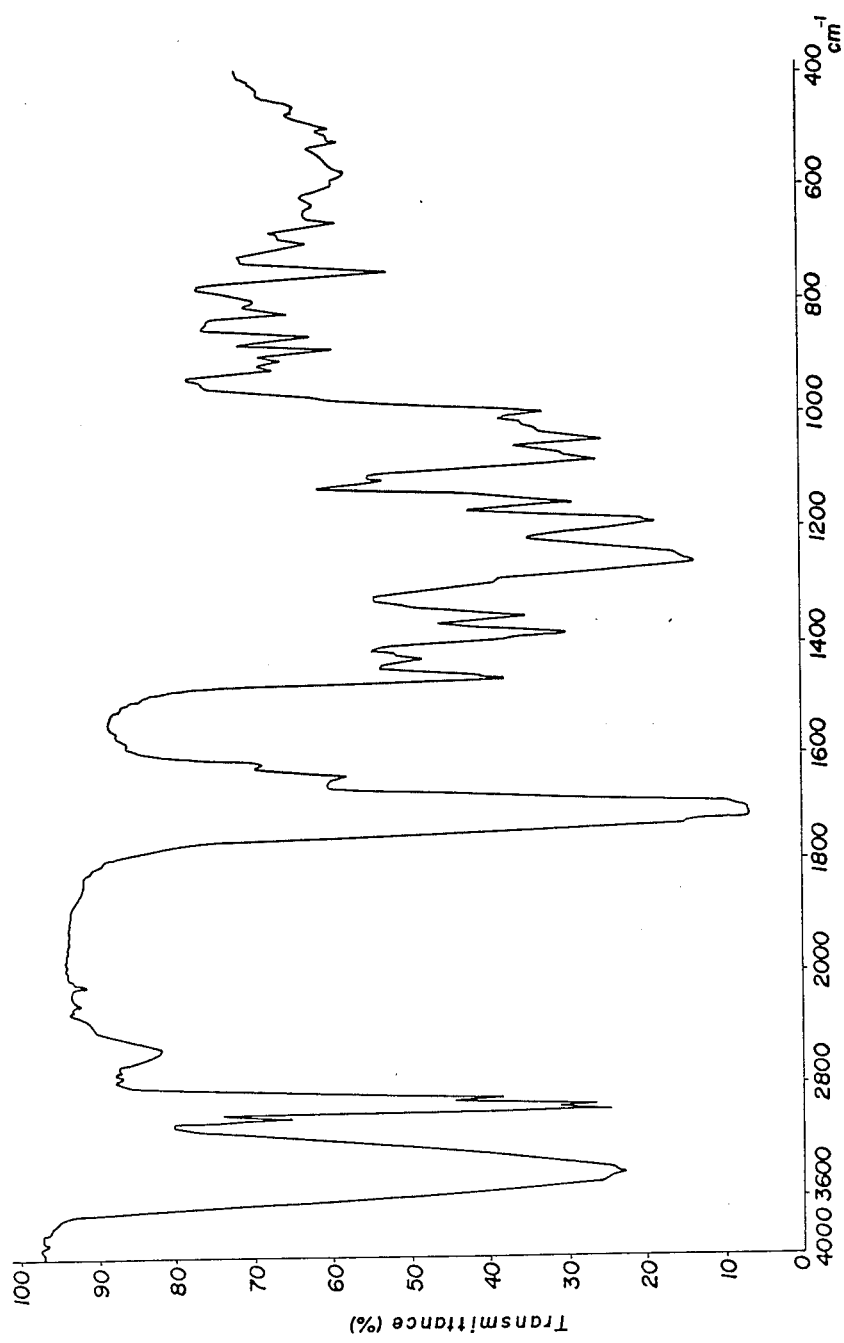

3. Infrared absorption spectrum (thin film):

The infrared absorption spectrum is shown in FIG. 2 of the accompanying drawings.

Preparation 2

Preparation of M-4

Figure 3:
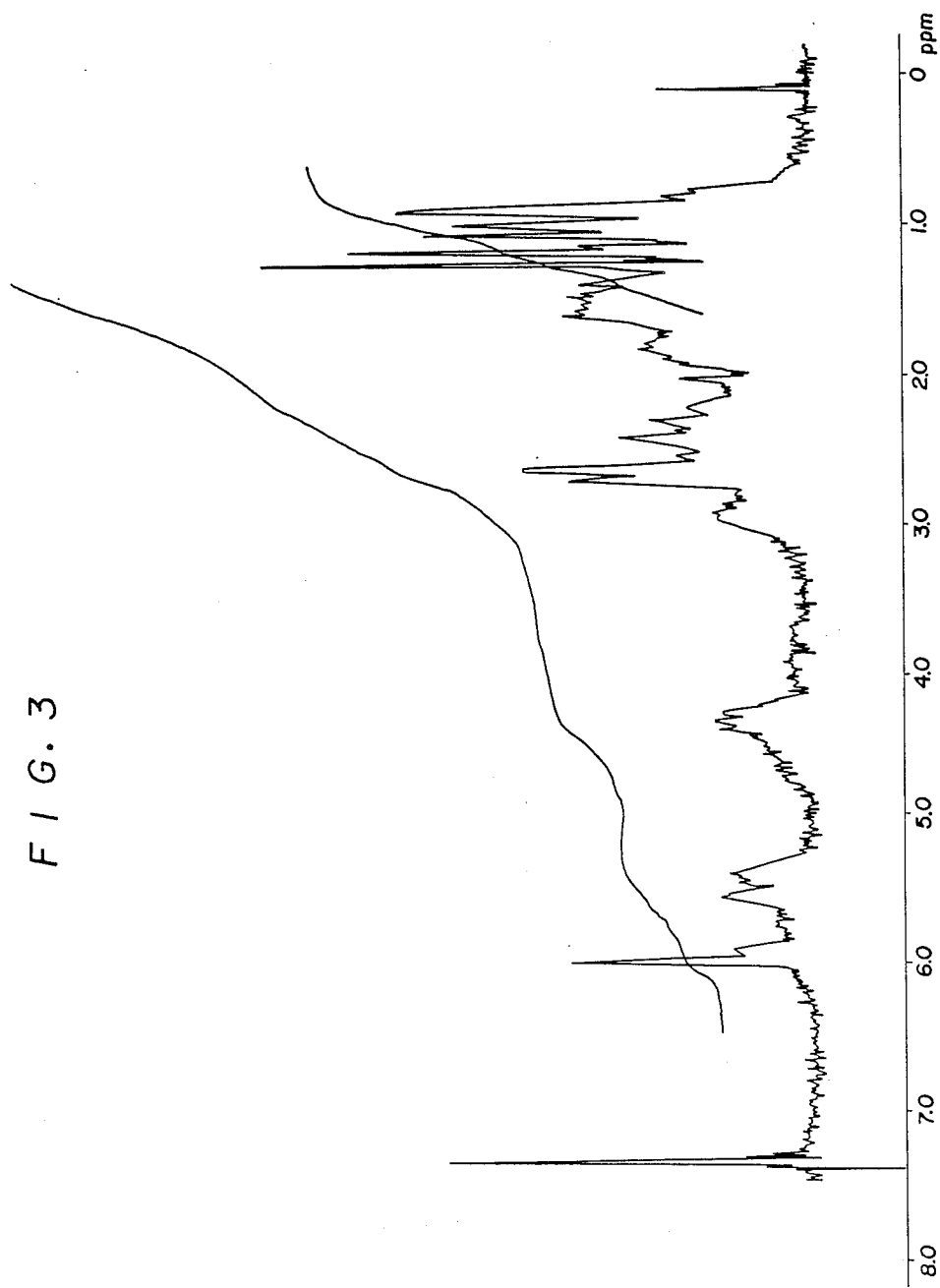

The procedure described in Preparation 1 was carried out up to and including elution of the first-mentioned Lobar column. After elution of the IsoM-4 lactone with the 1:1 by volume mixture of benzene and ethyl acetate, a further quantity of the same solvent mixture was used to elute the M-4 lactone, taking advantage of the difference in retention times between M-4 and IsoM-4. The resulting M-4 lactone solution was then treated as in Preparation 1, to give 98 mg of the desired M-4 lactone, having the following characteristics:

1. Nuclear magnetic resonance spectrum:

The nuclear magnetic resonance spectrum measured at 60 MHz in deuterochloroform using tetramethylsilane as the internal standard is shown in FIG. 3 of the accompanying drawings.

2. Ultraviolet absorption spectrum (methanol solution)

$\lambda_{max}$ nm: 230, 236.7, 244.6.

3. Infrared absorption spectrum (thin film) $\nu_{max}$ cm$^{-1}$: 3400, 2950, 1725.

4. Thin layer chromatography:

TLC plate: Merck silica gel Art 5715:

Solvent: benzene, acetone, acetic acid (50:50:3 by volume);

Rf value: 0.62.

EXAMPLE 1

Dihydro-Δ⁴-M-4 lactone

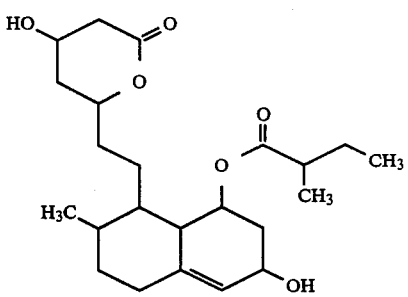

98 mg of a palladium catalyst comprising 5% by weight of palladium supported on barium sulphate were added to a solution of 3.9 g of M-4 in 100 ml of ethanol. The temperature of the reaction mixture was maintained at 25° C. under a stream of hydrogen. The supply of hydrogen was continued for 90 minutes, at which point its absorption ceased, after a molar equivalent of hydrogen had been absorbed. The catalyst residue was then filtered from the reaction mixture and the filtrate was concentrated by evaporation under reduced pressure, to give a clear oil. To this oil were added 50 ml of cyclohexane and 50 ml of hexane. The resulting solution was cooled to 5° C., whereupon a white powder precipitated. This white powder (totalling 2.5 g) was removed from the mother liquor (which was subsequently treated as described in Example 2).

The white powder was dissolved in a small amount of acetonitrile, and the resulting solution was passed through a Lobar column RP-8 and eluted with 40% v/v aqueous acetonitrile. The eluate was concentrated by evaporation under reduced pressure, to give 1.5 g of the title compound in the form of a white powder.

Elemental analysis: Calculated for $C_{23}H_{36}O_6$: C, 67.62%; H, 8.88%. Found: C, 68.05%; H, 8.32%.

Mass spectrum (M+): 408.

Infrared absorption spectrum (liquid film) $\nu_{max}$ cm$^{-1}$: 3450, 1730, 1670.

Nuclear magnetic resonance spectrum (60 MHz, CDCl₃) δ ppm: 5.60 (1H, multiplet); 5.33 (1H, singlet); 4.6 (1H, multiplet); 4.33 (1H, multiplet); 3.8 (1H, multiplet).

EXAMPLE 2

Dihydro-Δ⁴ᵃ-M-4

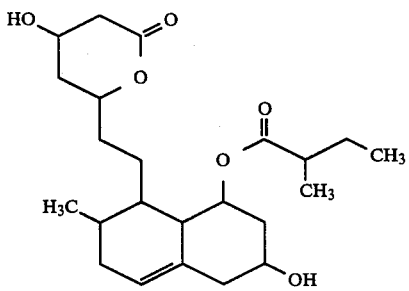

The mother liquor obtained in Example 1, after separation of the 2.5 g of white powder, was concentrated by evaporation under reduced pressure. The oil thus obtained was washed with hexane, giving 1.5 g of the title compound in the form of a colourless oil.

Elemental analysis: Calculated for $C_{23}H_{36}O_6$: C, 67.62%; H, 8.88%. Found: C, 67.39%; H, 8.55%.

Mass spectrum (M+): 408.

Infrared absorption spectrum (liquid film) $\nu_{max}$ cm$^{-1}$: 3400, 1720.

Nuclear magnetic resonance spectrum (60 MHz, CDCl₃) δ ppm: 5.61 (1H, multiplet); 5.33 (1H, singlet); 4.6 (1H, multiplet); 4.33 (1H, multiplet); 3.8 (H, multiplet).

EXAMPLE 3

Sodium dihydro-Δ⁴-M-4 carboxylate

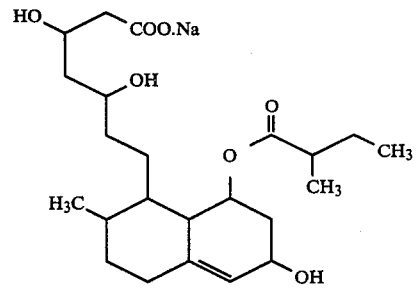

1.0 g of dihydro-Δ⁴-M-4, obtained as described in Example 1, was suspended in 50 ml of 50% v/v aqueous acetone. To the solution was added dropwise an equimolar amount of a 20% w/v aqueous solution of sodium hydroxide, over a period of about 2 hours to maintain the pH at a value below 12; meanwhile, the temperature of the solution was maintained at 40° C. When this reaction was complete, the pH of the reaction mixture was adjusted to about 8.5 by the addition of a small amount of 18% v/v hydrochloric acid, and then the acetone was distilled off under reduced pressure. The resulting residue was freeze-dried, to give 1.1 g of the title compound in the form of a hygroscopic powder.

Elemental analysis: Calculated for $C_{23}H_{37}O_7Na$: C, 61.61%; H, 8.26%; Na, 5.13%. Found: C, 60.79%; H, 8.52%; Na, 6.00%.

Molecular weight: 448 (by field desorption mass spectrum).

Infrared absorption spectrum (KBr) $\nu_{max}$ cm$^{-1}$: 3400, 1715, 1580.

Nuclear magnetic resonance spectrum (60 MHz, D₂O) δ ppm: 6.1 (1H, doublet); 5.8 (1H, singlet); 4.5 (1H, multiplet); 4.2 (1H, multiplet).

EXAMPLE 4

Sodium dihydro-Δ⁴ᵃ-M-4 carboxylate

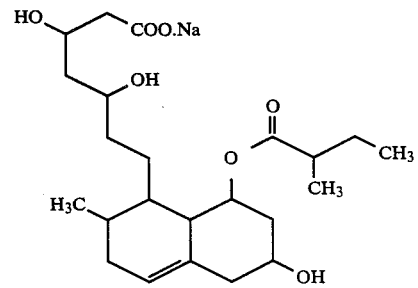

The procedure described in Example 3 was repeated, except that the dihydro-Δ⁴-M-4 was replaced by an equal amount of dihydro-Δ⁴ᵃ-M-4, giving 1.05 g of the title compound as a hygroscopic powder.

Elemental analysis: Calculated for $C_{23}H_{37}O_7Na$: C, 61.61%; H, 8.26%; Na, 5.13%. Found: C, 61.85%; H, 8.61%; Na, 5.64%.

Infrared absorption spectrum (KBr) $\nu_{max}$ cm⁻¹: 3410, 1720, 1580.

EXAMPLE 5

Calcium di(dihydro-Δ⁴-M-4 carboxylate)

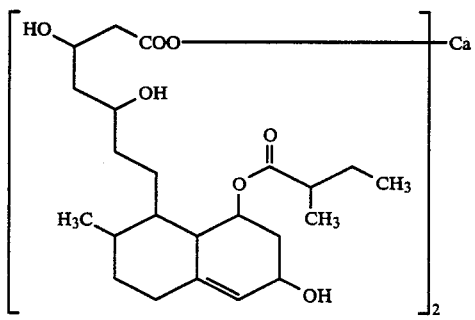

440 mg of dihydro-Δ⁴-M-4, obtained as described in Example 1, were suspended in 60 ml of 50% v/v aqueous acetone. The suspension was heated to 40° C., and then a 20% w/v aqueous solution of sodium hydroxide was added thereto dropwise, and the mixture was stirred at a pH value of 12 for 1 hour. The pH of the resulting mixture was then adjusted to a value of 7.5 by the addition of 18% v/v hydrochloric acid. To the resulting mixture was then added a solution of 120 mg of calcium chloride dihydrate in 10 ml of water, and the resulting calcium salt was extracted with ethylene dichloride. The extract was evaporated to dryness under reduced pressure, giving 270 mg of the title compound in the form of a white powder.

Elemental analysis: Calculated for $C_{46}H_{74}O_{14}Ca$: C, 62.02%; H, 8.31%. Found: C, 62.88%; H, 8.97%.

Infrared absorption spectrum (KBr) $\nu_{max}$ cm⁻¹: 3250, 1730.

EXAMPLE 6

Aluminum di(dihydro-Δ⁴-M-4carboxylate) hydroxide

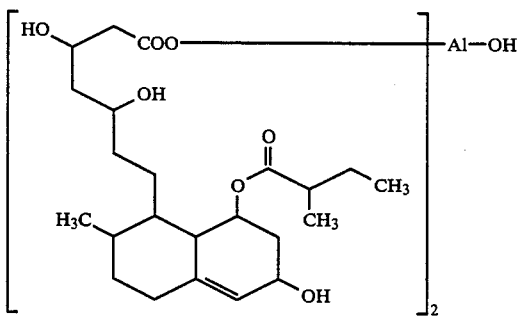

The procedure described in Example 5 was repeated, except that the calcium chloride dihydrate was replaced by an aqueous solution containing 90.2 mg of aluminium chloride hexahydrate. 485 mg of the title compound, in the form of a white powder, were obtained.

Elemental analysis: Calculated for $C_{46}H_{74}O_{14}Al$-(OH): C, 61.74%; H, 8.28%. Found: C, 61.98%; H, 8.52%.

Infrared absorption spectrum (KBr) $\nu_{max}$ cm⁻¹: 3360, 1730.

EXAMPLE 7 t-Octylamine dihydro-Δ⁴-M-4 carboxylate

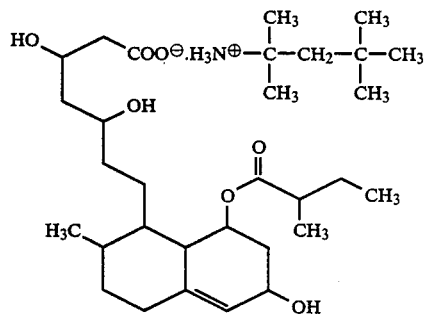

A solution of sodium dihydro-Δ⁴-M-4 carboxylate was prepared by saponification as described in Example 5 and was then cooled to 5° C. The pH of the solution was adjusted to a value of 4 by the addition of 18% v/v hydrochloric acid, and then sufficient t-octylamine was immediately added to the mixture to adjust its pH to a value of 7.8. After completion of the reaction, the acetone was distilled from the reaction mixture and the resulting residue was extracted with ethyl acetate. The extract was concentrated by evaporation under reduced pressure and then hexane was added to the resulting residue, to precipitate 440 mg of the title compound in the form of a white powder.

Elemental analysis: Calculated for $C_{31}H_{57}O_7N$: C, 67.02%; H, 10.27%; N, 2.52%. Found: C, 66.89%; H, 10.38%; N, 2.38%.

Infrared absorption spectrum (KBr) $\nu_{max}$ cm⁻¹: 3490, 1725.

EXAMPLE 8

D(-)-Phenylglycine methyl ester dihydro-Δ⁴-M-4 carboxylate

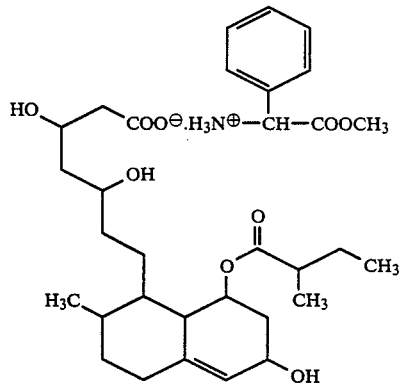

A solution of sodium dihydro-Δ⁴-M-4 carboxylate was prepared by saponification as described in Example 5. Then, instead of adding the calcium chloride dihydrate, 230 mg of D(-)-phenylglycine methyl ester hydrochloride were added, whereupon the pH of the solution changed from a value of 8.5 to a value of 6.2. Upon completion of the reaction, the reaction mixture was extracted with ethylene dichloride, and then the extract was evaporated to dryness under reduced pressure, to give 435.2 mg of the title compound in the form of an oil.

Elemental analysis: Calculated for $C_{32}H_{49}O_9N$: C, 64.97%; H, 8.29%; N, 2.37%. Found: C, 65.51%; H, 8.61%; N, 2.66%.

Infrared absorption spectrum (liquid film) $\nu_{max}$ cm$^{-1}$: 3300, 1700–1760.

Nuclear magnetic resonance spectrum (60 MHz, 0.5 ml $CDCl_3 + drop$ $D_2O$) δ ppm: 7.30 (5H, singlet); 5.20–5.60 (2H, multiplet); 3.70 (3H, singlet).

EXAMPLE 9

D(-)-Phenylglycine ethyl ester dihydro-$\Delta^4$-M-4 carboxylate

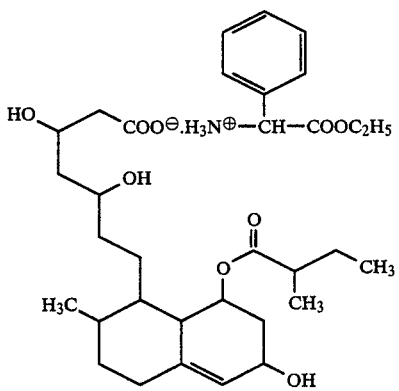

The procedure described in Example 7 was repeated, except that the t-octylamine was replaced by 210 mg of D(-)-phenylglycine ethyl ester. The resulting residue was extracted with chloroform, and then the extract was evaporated to dryness under reduced pressure, to give 501 mg of the desired product in the form of an oil.

Elemental analysis: Calculated for $C_{33}H_{51}O_9N$: C, 65.45%; H, 8.43%; N, 2.31%. Found: C, 65.90%; H, 8.85%; N, 2.63%.

Infrared absorption spectrum (liquid film) $\nu_{max}$ cm$^{-1}$: 3340, 3280, 1740, 1725.

Nuclear magnetic resonance spectrum (60 MHz, 0.5 ml $CDCl_3$+drop $D_2O$) δ ppm: 7.2 (5H, singlet); 5.60–5.15 (2H, multiplet); 4.05 (2H, quartet).

EXAMPLE 10

L-Ornithine dihydro-$\Delta^4$-M-4 carboxylate

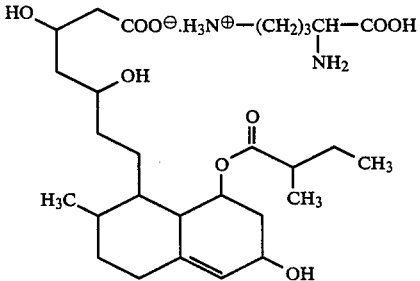

A solution of sodium dihydro-$\Delta^4$-M-4 carboxylate was prepared by saponification, as described in Example 5; then, in place of the calcium chloride dihydrate, 195 mg of L-ornithine hydrochloride were added, whereupon the pH changed from a value of 8.5 to a value of 7.0. Upon completion of the reaction, the acetone was distilled from the reaction mixture under reduced pressure, and then the resulting aqueous solution was passed through a column containing 10 ml of a highly porous absorbent resin (Diaion HP-20, a trade mark), and it was then eluted with 40% v/v aqueous methanol. The eluate was concentrated by evaporation under reduced pressure and then freeze-dried, giving 375 mg of the title compound in the form of a white powder.

Elemental analysis: Calculated for $C_{28}H_{50}O_9N_2$: C, 60.22%; H, 8.96%; N, 5.02%. Found: C, 60.61%; H, 9.33%; N, 5.41%.

Infrared absorption spectrum (Nujol—trade mark) $\nu_{max}$ cm$^{-1}$: 3400, 1725.

EXAMPLE 11

Methyl dihydro-$\Delta^4$-M-4 carboxylate

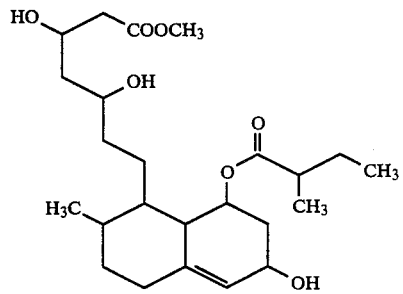

690 mg of sodium dihydro-$\Delta^4$-M-4 carboxylate, prepared as described in Example 3, were dissolved in 5 ml of dimethylformamide. To this solution were added 100 mg of potassium carbonate and 290 mg of methyl iodide (95% purity), after which the mixture was stirred at room temperature for 3 hours. At the end of this time, water was added to the reaction mixture, which was then extracted with ethyl acetate. The extract was concentrated by evaporation under reduced pressure, to give an oily substance, which was then purified using a Lobar column RP-8, eluted with 60% v/v aqueous acetonitrile, to give 380 mg of the title compound in the form of an oil.

Elemental analysis: Calculated for $C_{24}H_{40}O_7$: C, 65.43%; H, 9.15%. Found: C, 64.96%; H, 8.90%.

Mass spectrum (M+): 440.

Infrared absorption spectrum (liquid film ) $\nu_{max}$ cm$^{-1}$: 3400, 1730.

Nuclear magnetic resonance spectrum (60 MHz, $CDCl_3$) δ ppm: 5.30–5.60 (2H, multiplet); 4.2 (1H, multiplet); 3.70 (3H, singlet).

EXAMPLE 12

Butyl dihydro-$\Delta^4$-M-4 carboxylate

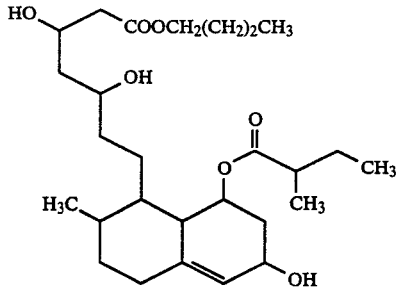

The procedure described in Example 11 was repeated, except that the methyl iodide was replaced by 260 mg of butyl bromide. There were obtained 310 mg of the desired compound in the form of an oil.

Elemental analysis: Calculated for $C_{27}H_{46}O_7$: C, 67.22%; H, 9.54%. Found: C, 67.51%; H, 9.78%.

Mass spectrum ($M^{30}$): 482.

Infrared absorption spectrum (liquid film) $\nu_{max}$ cm$^{-1}$: 3380, 1725.

Nuclear magnetic resonance spectrum (60 MHz, CDCl$_3$) $\delta$ ppm: 5.15–5.60 (2H, multiplet); 4.22 (1H, multiplet); 4.10 (2H, triplet).

EXAMPLE 13

Benzyl dihydro-$\Delta^4$-M-4 carboxylate

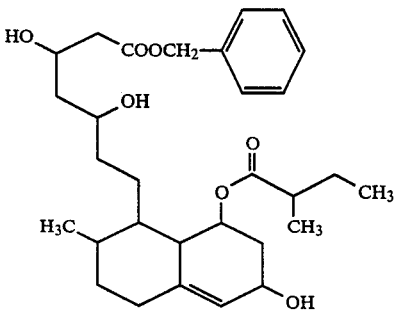

The procedure described in Example 11 was repeated, except that the methyl iodide was replaced by 355 mg of benzyl bromide. 610 mg of the title compound, in the form of an oil, were obtained.

Elemental analysis: Calculated for $C_{30}H_{44}O_7$: C, 69.77%; H, 8.53%. Found: C, 70.10%; H, 8.92%.

Mass spectrum ($M^+$): 516.

Infrared absorption spectrum (liquid film)$\nu_{max}$ cm$^{-1}$: 3420, 1725.

Nuclear magnetic resonance spectrum (60 MHz, CDCl$_3$)$\delta$ ppm: 7.30 (5H, singlet); 5.15–5.50 (2H, multiplet); 5.10 (2H, singlet).

EXAMPLE 14

4-Bromophenacyl dihydro-$\Delta^4$-M-4 carboxylate

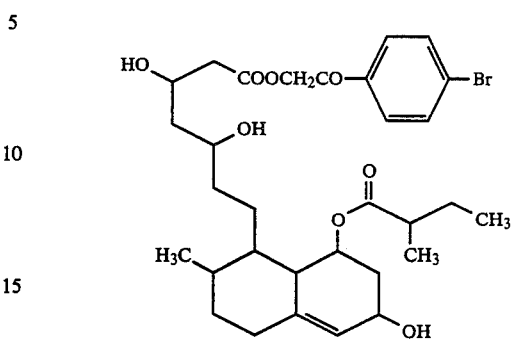

The procedure described in Example 11 was repeated, except that the methyl iodide was replaced by 560 mg of 4-bromophenacyl bromide. 755 mg of the title compound were obtained, in the form of a slightly yellow oil.

Elemental analysis: Calculated for $C_{31}H_{43}O_8Br$: C, 59.71%; H, 6.90%; 12.84%. Found: C, 61.05%; H, 7.12%; Br, 13.15%.

Mass spectrum ($M^+$, as $Br^{79}$): 622.

Infrared absorption spectrum (liquid film)$\nu_{max}$ cm$^{-1}$: 3420, 1745, 1730, 1710.

Nuclear magnetic resonance spectrum (60 MHz, CDCl$_3$)$\delta$ ppm: 7.70 (4H, multiplet); 5.35 (2H, singlet); 5.15–5.55 (2H, multiplet).

EXAMPLE 15

Dihydro-$\Delta^4$-IsoM-4 lactone

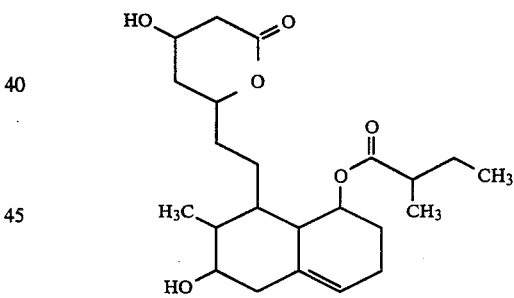

To a solution of 3.27 g of IsoM-4 in 100 ml of ethanol were added 65 mg of a palladium catalyst, comprising 5% w/w palladium supported on barium sulphate.

The catalytic reduction reaction was carried out under a stream of hydrogen at atmospheric pressure and at 25° C. This was continued until absorption of hydrogen ceased, which took about 60 minutes, whereupon a molar equivalent of hydrogen had been absorbed. The catalyst was then filtered from the reaction mixture and the filtrate was concentrated by evaporation under reduced pressure, to give a clear oil. To this oil were added 15 ml of cyclohexane and 20 ml of hexane, to make a solution. This solution was cooled to 5° C. and the white powder which precipitated (a total of 2.0 g) was separated from the mother liquor. The mother liquor was treated as described in Example 16.

The white powder was dissolved in a small quantity of acetonitrile and purified by elution through a Lobar column RP-8, eluted with 40% v/v aqueous acetonitrile, to give 800 mg of the desired product in the form of white crystals.

Elemental analysis: Calculated for $C_{23}H_{36}O_6$: C, 67.62%; H, 8.88%. Found: C, 67.91%; H, 9.21%.

Mass spectrum (M+): 408.

Infrared absorption spectrum (liquid film)$\nu_{max}$ cm$^{-1}$: 3450, 1735, 1680.

Nuclear magnetic resonance spectrum (60 MHz, CDCl$_3$)$\delta$ ppm; 5.65 (1H, multiplet); 5.40 (1H, multiplet); 4.61 (1H, multiplet); 4.40 (1H, multiplet); 3.80 (1H, multiplet).

EXAMPLE 16

Dihydro-$\Delta^{4a}$-IsoM-4 lactone

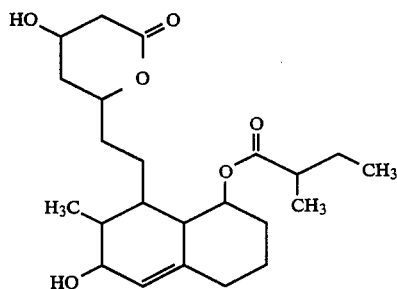

The mother liquor prepared in Example 15, after separation of the 2.0 g of white powder, was concentrated by evaporation under reduced pressure. The resulting oil was washed with hexane, giving 1.2 g of the desired compound in the form of a colourless oil.

Elemental analysis: Calculated for $C_{23}H_{36}O_6$: C, 67.62%; H, 8.88%; Found: C, 67.82%; H, 8.98%.

Mass spectrum (M+): 4.08.

Infrared absorption spectrum (liquid film)$\nu_{max}$ cm$^{-1}$: 3400, 1720.

Nuclear magnetic resonance spectrum (60 MHz, CDCl$_3$)$\delta$ ppm: 5.65 (1H, multiplet); 5.40 (1H, multiplet); 4.6 (1H, multiplet); 4.3 (1H, multiplet); 3.8 (1H, multiplet).

EXAMPLE 17

Sodium dihydro-$\Delta^4$-IsoM-4 carboxylate

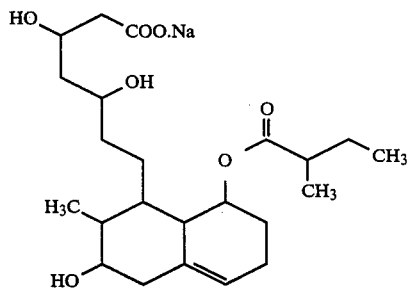

3 g of dihydro-$\Delta^4$-IsoM-4, prepared as described in Example 15, were suspended in 100 ml of 50% v/v aqueous acetone. The suspension was maintained at 40° C., whilst an equimolar amount of a 20w/v aqueous solution of sodium hydroxide was added dropwise over about 3 hours at a rate sufficient to maintain the mixture at a pH value of about 12. Upon completion of the reaction, the pH value of the reaction mixture was adjusted to 8.5 by the addition of a small quantity of 18% v/v hydrochloric acid, and then the acetone was distilled off under reduced pressure. The resulting residue was freeze-dried, to give 3.3 of the title compound in the form of a hygroscopic powder.

Elemental analysis: Calculated for $C_{23}H_{37}O_7Na$: C, 61.61%; H, 8.26%; Na, 5.13%. Found: C, 61.85%; H, 8.56%; Na, 5.49%.

Infrared absorption spectrum (KBr)$\nu_{max}$ cm$^{-1}$: 3280, 1725.

EXAMPLE 18

Sodium dihydro-$\Delta^{4a}$-IsoM-4 carboxylate

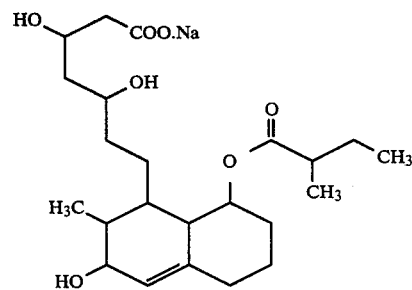

The procedure described in Example 17 was repeated, except that the dihydro-$\Delta^4$-IsoM-4 was replaced by an equal amount of dihydro-$\Delta^{4a}$-IsoM-4. There were obtained 3.2 g of the title compound in the form of a hygroscopic powder.

Elemental analysis: Calculated for $C_{23}H_{37}O_7Na$; C, 61.61%; H, 8.26%; Na, 5.13%. Found: C, 61.52%, H, 8.01%; Na, 5.41%.

Infrared absorption spectrum (KBr)$\nu_{max}$ cm$^{-1}$: 3275, 1730.

EXAMPLE 19

Calcium di(dihydro-$\Delta^4$-IsoM-4 carboxylate

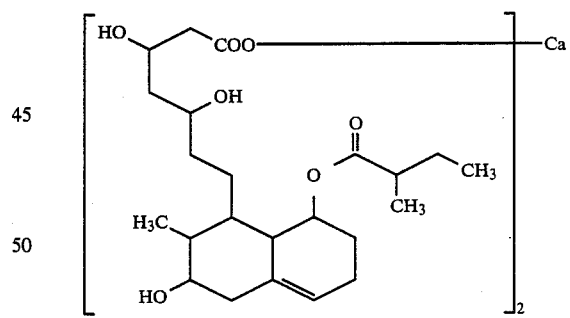

440 mg of dihydro-$\Delta^4$-IsoM-4, prepared as described in Example 15, were suspended in 60 ml of 50% v/v aqueous acetone. The suspension was heated to 40° C., and then a 20% w/v aqueous solution of sodium hydroxide as added dropwise thereto, after which the mixture was stirred at a pH value of 12 for 1 hour. The pH of the mixture was adjusted to a value of 8.5 by the addition of 18% v/v hydrochloric acid, and then a solution of 120 mg of calcium chloride dihydrate in 10 ml of water was added. The resulting calcium salt was extracted with ethylene dichloride. The extract was concentrated by evaporation under reduced pressure, to give 370 mg of the title compound in the form of a white powder.

Elemental analysis: Calculated for $C_{46}H_{74}O_{14}Ca$: C, 62.02%; H, 8.31%; Found: C, 61.77%; H, 8.54%.

Infrared absorption spectrum (KBr)$\nu_{max}$ cm$^{-1}$: 3420, 1715.

EXAMPLE 20

Aluminium di(dihydro-Δ$^4$-IsoM-4 carboxylate) hydroxide

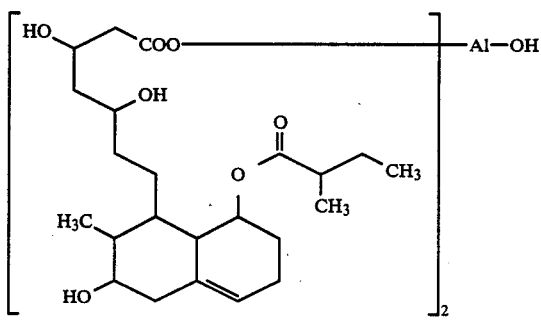

The procedure described in Example 6 was repeated, except that a solution of sodium dihydro-Δ$^4$-IsoM-4 carboxylate (prepared by saponification, as described in Example 19) was used in place of the solution of sodium dihydro-Δ$^4$-M-4 carboxylate and 91.5 mg of aluminium chloride hexahydrate were used. 480 mg of the title compound, in the form of a white powder, were obtained.

Elemental analysis: Calculated for $C_{46}H_{74}O_{14}Al(OH)$: C, 61.74%; H, 8.28%. Found: C, 61.12%; H, 9.01%.

Infrared absorption spectrum (KBr)$\nu_{max}$ cm$^{-1}$: 3350, 1725.

EXAMPLE 21 t-Octylamine dihydro-Δ$^4$-IsoM-4 carboxylate

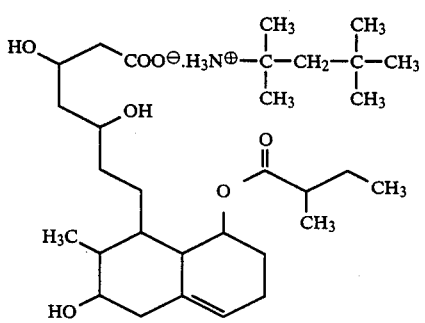

A solution of sodium dihydro-Δ$^4$-IsoM-4 carboxylate (prepared by saponification, as described in Example 19) was cooled to 5° C. The pH of the solution was adjusted to a value of 4.0 by the addition of 18% v/v hydrochloric acid, and then sufficient t-octylamine was immediately added to adjust the pH to a value of 7.8. Upon completion of the reaction, the acetone was distilled from the reaction mixture under reduced pressure and the resulting residue was extracted with ethyl acetate. The extract was concentrated by evaporation under reduced pressure and the resulting residue was crystallised from hexane, to give 430 mg of the title compound in the form of a white powder.

Elemental analysis:

Calculated for $C_{31}H_{57}O_7N$: C, 67.03%; H, 10.27%; N, 2.52%. Found: C, 67.45%; H, 10.54%; N, 2.46%.

Infrared absorption spectrum (KBr)$\nu_{max}$ cm$^{-1}$: 3480, 1725.

EXAMPLE 22

D(−)-Phenylglycine methyl ester dihydro-Δ$^4$-IsoM-4 carboxylate

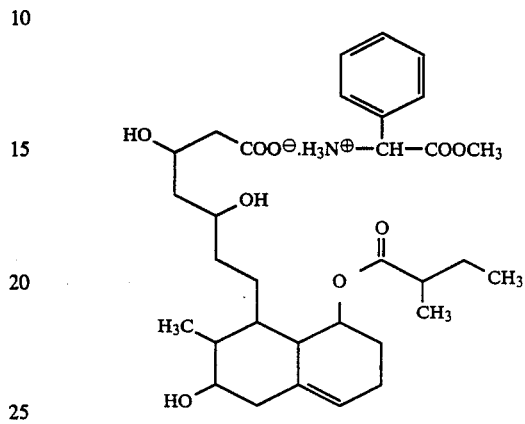

A solution of sodium dihydro-Δ$^4$-IsoM-4 carboxylate was prepared by saponification, as described in Example 19; then, instead of adding calcium chloride dihydrate, 227 mg of D(−)-phenylglycine methyl ester hydrochloride were added, whereupon the pH value of the mixture changed from 8.5 to 6.2. Upon completion of the reaction, the reaction mixture was extracted with ethylene dichloride. The extract was evaporated to dryness under reduced pressure, to give 433 mg of the title compound in the form of an oil.

Elemental analysis: Calculated for $C_{33}H_{49}O_9N$: C, 64.97%; H, 8.29%; N, 2.37%. Found: C, 64.58%; H, 8.45%; N, 2.33%.

Infrared absorption spectrum (liquid film)$\nu_{max}$ cm$^{-1}$: 3300, 1700–1760.

Nuclear magnetic resonance spectrum (60 MHz, 0.5 ml CDCl$_3$+drop D$_2$O) δ ppm: 7.30 (5H, singlet); 5.20–5.60 (2H, multiplet); 3.70 (3H, singlet).

EXAMPLE 23

D(−)-Phenylglycine ethyl ester dihydro-Δ$^4$-IsoM-4 carboxylate

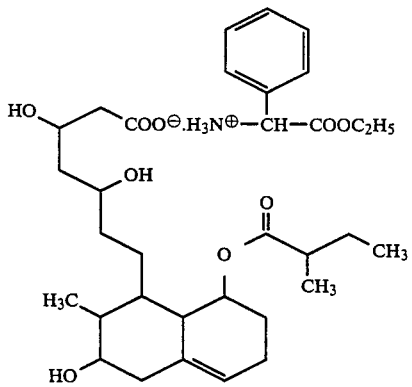

The procedure described in Example 21 was repeated, except that the t-octylamine was replaced by 201 mg of D(−)-phenylglycine ethyl ester. The resulting residue was extracted with chloroform, and the extract was evaporated under reduced pressure, to give 497 mg of the desired compound in the form of an oil.

Elemental analysis: Calculated for $C_{33}H_{51}O_9N$: C, 65.45%, H, 8.43%; N, 2.31%. Found: C, 65.11%; H, 8.15%; N, 2.71%.

Infrared absorption spectrum (liquid film)$\nu_{max}cm^{-1}$: 3340, 3280, 1735, 1720.

Nuclear magntic resonance spectrum (60 MHz, 0.5 ml $CDCl_3$+drop $D_2O$)δppm: 7.30 (5H, singlet); 5.60–5.15 (2H, multiplet); 4.15 (2H, quartet).

EXAMPLE 24

L-Ornithine dihydro-$\Delta^4$-IsoM-4 carboxylate

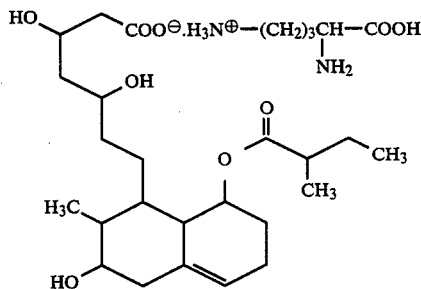

A solution of sodium dihydro-$\Delta^4$-IsoM-4 carboxylate was prepared by saponification, as described in Example 19; then, instead of adding the calcium chloride dihydrate, 192 mg of L-ornithine hydrochloride were added, whereupon the pH value of the mixture changed from 8.5 to 7.0. Upon completion of the reaction, the acetone was distilled off under reduced pressure and the resulting aqueous solution was adsorbed on a column charged with 10 ml of a highly porous adsorbent resin (Diaion HP-20), and eluted with 50% v/v aqueous methanol. The eluate was concentrated by evaporation under reduced pressure and the residue was freeze-dried to give 385 mg of the title compound in the form of a white powder.

Elemental analysis: Calculated for $C_{28}H_{50}O_9N_2$: C, 60.22%; H, 8.96%; N, 5.02%. Found: C, 60.11%; H, 8.62%; N, 4.71%.

Infrared absorption spectrum (KBr)$\nu_{max}cm^{-1}$: 3350, 1725.

EXAMPLE 25

Methyl dihydro-$\Delta^4$-IsoM-4 carboxylate

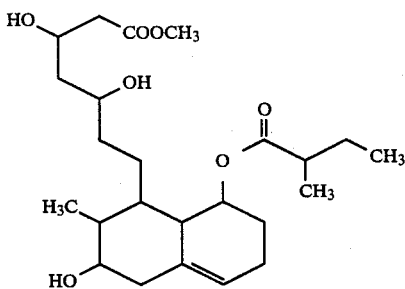

690 mg of sodium dihydro-$\Delta^4$-IsoM-4 carboxylate, prepared as described in Example 17, were dissolved in 5 ml of dimethylformamide. 100 mg of potassium carbonate and 280 mg of methyl iodide (95% purity) were then added to the solution and the resulting mixture was stirred at room temperature for 3 hours. After completion of the reaction, water was added to the reaction mixture, and then the mixture was extracted with ethyl acetate. The extract was concentrated by evaporation under reduced pressure and the resulting residue was purified by chromatography through a Lobar column RP-8, eluted with 60% v/v aqueous acetonitrile, to give 400 mg of the title compound in the form of an oil.

Elemental analysis: Calculated for $C_{24}H_{40}O_7$: C, 65.45%; H, 9.09%. Found: C, 65.12%; H, 9.22%.

Mass spectrum (M+): 440.

Infrared absorption spectrum (liquid film)$\nu_{max}cm^{-1}$: 3350, 1725.

Nuclear magnetic resonance spectrum (60 MHz, $CDCl_3$)δppm: 5.15–5.50 (2H, multiplet); 3.70 (3H, singlet).

EXAMPLE 26

Butyl dihydro-$\Delta^4$-IsoM-4 carboxylate

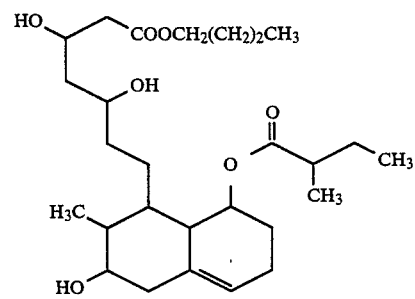

The procedure described in Example 25 was repeated, except that the methyl iodide was replaced by 270 mg of butyl bromide. 325 mg of the title compound, in the form of an oil, were obtained.

Elemental analysis; Calculated for $C_{27}H_{46}O_7$: C, 67.22%; H, 9.54%. Found: C, 67.04%; H, 9.78%.

Mass spectrum (M+): 482.

Infrared absorption spectrum (liquid film)$\nu_{max}cm^{-1}$: 3330, 1715.

Nuclear magnetic resonance spectrum (60 MHz, $CDCl_3$)δppm: 5.15–5.60 (2H, multiplet); 4.10 (2H, triplet).

EXAMPLE 27

Benzyl dihydro-$\Delta^4$-IsoM-4 carboxylate

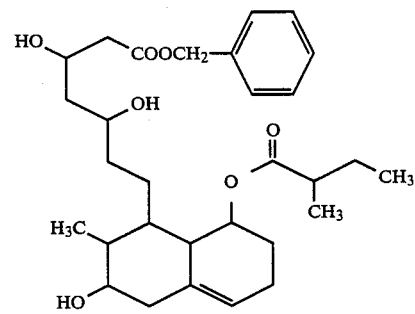

The procedure described in Example 25 was repeated, except that the methyl iodide was replaced by 370 mg of benzyl bromide. 600 mg of the title compound were obtained, in the form of an oil.

Elemental analysis: Calculated for $C_{30}H_{44}O_7$: C, 69.77%; H, 8.53%. Found: C, 69.52%; H, 8.77%.

Mass spectrum (M+): 516.

Infrared absorption spectrum (liquid film)$\nu_{max}$cm$^{-1}$: 3400, 1720.

Nuclear magnetic resonance spectrum (60 MHz, CDCl$_3$)$\delta$ppm: 7.30 (5H, singlet); 5.15–5.50 (2H, multiplet); 5.10 (2H, singlet).

EXAMPLE 28

4-Bromophenacyl dihydro-$\Delta^4$-IsoM-4 carboxylate

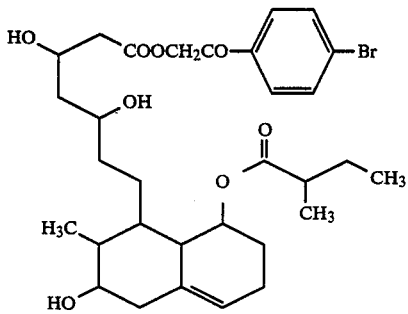

The procedure described in Example 25 was repeated, except that the methyl iodide was replaced by 595 mg of 4-bromophenacyl bromide. 785 mg of the title compound were obtained, in the form of a slightly yellow oil.

Elemental analysis: Calculated for $C_{31}H_{43}O_8Br$: C, 59.71%; H, 6.90%; Br, 12.84%. Found: C, 59.58%; H, 7.23%; Br, 13.01%.

Mass spectrum (M+, as Br$^{79}$): 622.

Infrared absorption spectrum (liquid film)$\nu_{max}$cm$^{-1}$: 3420, 1745, 1730, 1710.

Nuclear magnetic resonance spectrum (60 MHz, CDCl$_3$)$\delta$ppm: 7.70 (4H, multiplet); 5.35 (2H, singlet); 5.15–5.55 (2H, multiplet).

We claim:

1. Compounds of formula (V):

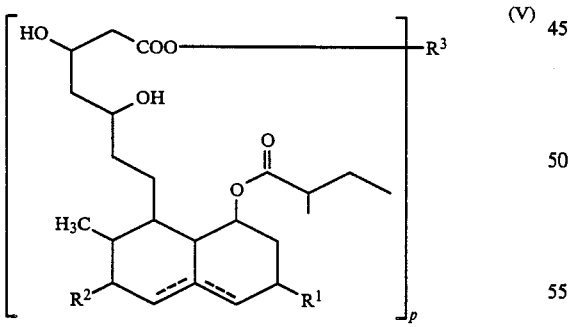

wherein:
one of $R^1$ and $R^2$ represents a hydrogen atom and the other represents a hydroxy group;
$R^3$ represents a group selected from the group consisting of $C_1$-$C_6$ alkyl, benzyl, benzyl substituted with at least one substituent selected from the group consisting of $C_1$-$C_2$ alkyl, $C_1$-$C_2$ alkoxy and halogen, phenacyl, and phenacyl substituted with at least one substituent selected from the group consisting of $C_1$-$C_2$ alkyl, $C_1$-$C_2$ alkoxy and halogen;

the structure shown as

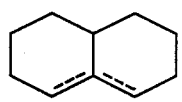

represents a structure of formula

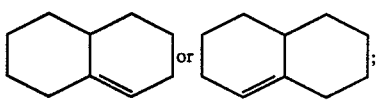

and
p is 1.

2. Compounds of formula (III):

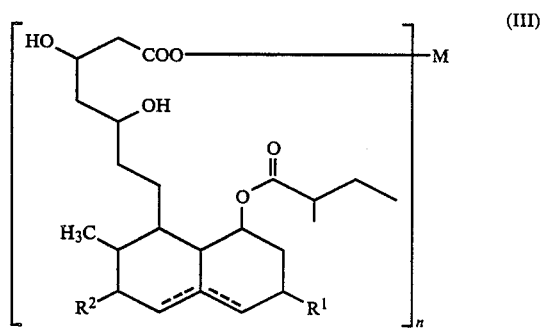

wherein:
one of $R^1$ and $R^2$ represents a hydrogen atom and the other represents a hydroxy group;
the structure shown as

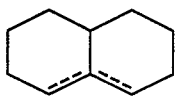

represents a structure of formula

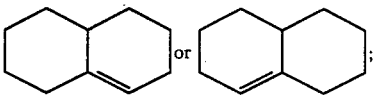

M represents a metal atom selected from the group consisting of alkali metals, alkaline earth metals, aluminum, iron, zinc, nickel and cobalt; and
n represents the valency of the metal atom M.

3. Compounds as claimed in claim 2, wherein M represents a metal selected from the group consisting of sodium, potassium, calcium, magnesium, aluminium, iron, zinc, copper, nickel and cobalt.

4. Compounds as claimed in claim 2, wherein M represents a metal selected from the group consisting of sodium, calcium and aluminium.

5. The dihydro-M-4 and dihydro-IsoM-4 compounds of formula (IV):

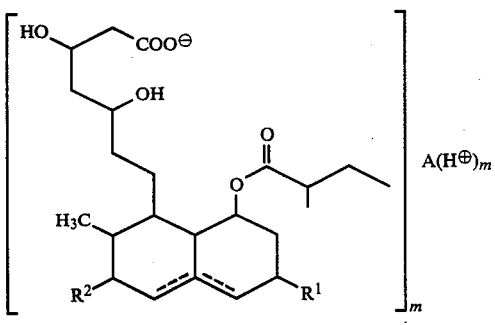

(IV)

wherein:
one of $R^1$ and $R^2$ represents a hydrogen atom and the other represents a hydroxy group;
the structure shown as

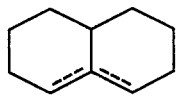

represents a structure of formula

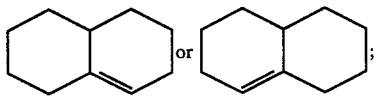

A represents ammonia or an organic amine; and m is an integer.

6. Compounds as claimed in claim 5, wherein A represents a basic amino acid selected from the group consisting of arginine, lysine, histidine, 2,4-diaminobutyric acid and ornithine.

7. Compounds as claimed in claim 5, wherein A represents ammonia.

8. Compounds as claimed in claim 5, wherein A represents an organic amine selected from the group consisting of t-octylamine, benzylamine, dibenzylamine, N,N-dimethylbenzylamine, cyclohexylamine, dicyclohexylamine, N,N-dimethylcyclohexylamine, N-methylpyrrolidine, morpholine, L-leucine alkyl esters, dialkyl L-glutamates, D-phenylglycine alkyl esters and D-glucosamine.

9. Compounds as claimed in claim 5, wherein A represents an organic amine selected from the group consisting of t-octylamine, dibenzylamine, dicyclohexylamine, morpholine, D-phenylglycine alkyl esters and D-glucosamine.

10. Compounds as claimed in claim 1, wherein $R^3$ represents a $C_1$–$C_6$ alkyl group, a benzyl group, a benzyl group having a single substituent selected from $C_1$–$C_2$ alkyl or alkoxy groups and halogen atoms, a phenacyl group or a phenacyl group having a single substituent selected from $C_1$–$C_2$ alkyl or alkoxy groups and halogen atoms.

11. Compounds as claimed in claim 5 wherein A is an amino acid.

12. A pharmaceutical composition comprising an effective amount of an antihyperlipaemic agent, in admixture with a pharmaceutically acceptable carrier or diluent, wherein the antihyperlipaemic agent is selected from dihydro-M-4 and dihydro-IsoM-4 hydroxy carboxylic acids of formula (II):

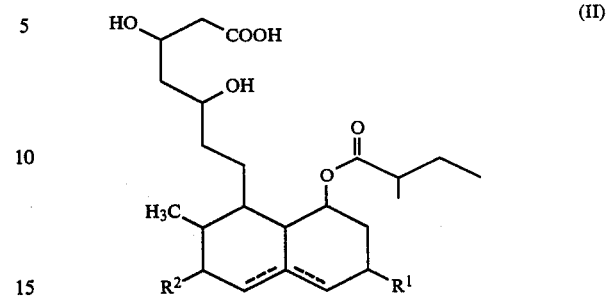

(II)

wherein one of $R^1$ and $R^2$ represents a hydrogen atom and the other represents a hydroxy group and wherein the structure shown as

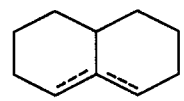

represents a structure of formula

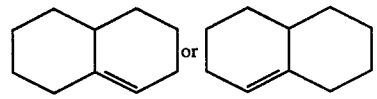

and the salts and esters of said acids, said esters being the compounds wherein the acid hydrogen atom is replaced with a group selected from the group consisting of $C_1$–$C_6$ alkyl, benzyl, benzyl substituted with at least one substituent selected from the group consisting of $C_1$–$C_2$ alkyl, $C_1$–$C_2$ alkoxy and halogen, phenacyl, and phenacyl substituted with at least one substituent selected from the group consisting of $C_1$–$C_2$ alkyl, $C_1$–$C_2$ alkoxy and halogen.

13. A composition as claimed in claim 12, wherein said antihyperlipaemic agent is selected from the group consisting of dihydro-M-4 carboxylic acids, dihydro-IsoM-4 carboxylic acids, sodium dihydro-M-4 carboxylates and sodium dihydro-IsoM-4 carboxylates.

14. The dihydro-M-4 and dihydro-IsoM-4 hydroxy carboxylic acids of the formula (II):

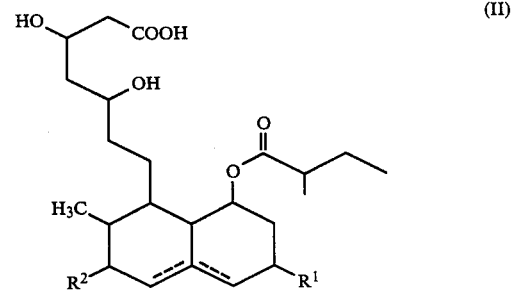

(II)

wherein one of $R^1$ and $R^2$ represents a hydrogen atom and the other represents a hydroxy group and wherein the structure shown as

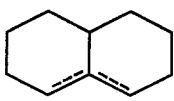

represents a structure of formula

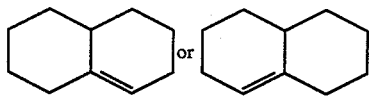

and the salts and esters of said acids, said esters being the compounds.
wherein the acid hydrogen atom is replaced with a group selected from the group consisting of $C_1$–$C_6$ alkyl, benzyl, benzyl substituted with at least one substituent selected from the group consisting of $C_1$–$C_2$ alkyl, $C_1$–$C_2$ alkoxy and halogen, phenacyl, and phenacyl substituted with at least one substituent selected from the group consisting of $C_1$–$C_2$ alkyl, $C_1$–$C_2$ alkoxy and halogen.

15. Dihydro-$\Delta^4$-M-4 carboxylic acid of the formula of claim 14.

16. Dihydro-$\Delta^4$-IsoM-4 carboxylic acid of the formula of claim 14.

17. Sodium dihydro-$\Delta^4$-M-4 carboxylate of the formula of claim 14.

18. Sodium dihydro-$\Delta^4$-IsoM-4 carboxylate of the formula of claim 14.

19. Dihydro-$\Delta^{4a}$-M-4 carboxylic acid of the formula of claim 14.

20. Dihydro-$\Delta^{4a}$-IsoM-4 carboxylic acid of the formula of claim 14.

21. Sodium dihydro-$\Delta^{4a}$-M-4 carboxylate of the formula of claim 14.

22. Sodium dihydro-$\Delta^{4a}$-IsoM-4 carboxylate of the formula of claim 14.

* * * * *